United States Patent
Osman (10) Patent No.: US 12,178,511 B2
(45) Date of Patent: Dec. 31, 2024

(54) EYE TRACKING FOR ACCESSIBILITY AND VISIBILITY OF CRITICAL ELEMENTS AS WELL AS PERFORMANCE ENHANCEMENTS

(71) Applicant: Sony Interactive Entertainment Inc., Tokyo (JP)

(72) Inventor: Steven Osman, San Mateo, CA (US)

(73) Assignee: Sony Interactive Entertainment Inc., Tokyo (JP)

( * ) Notice: Subject to any disclaimer, the term of this patent is extended or adjusted under 35 U.S.C. 154(b) by 330 days.

(21) Appl. No.: 17/817,183

(22) Filed: Aug. 3, 2022

(65) Prior Publication Data
US 2024/0041319 A1 Feb. 8, 2024

(51) Int. Cl.
| | |
|---|---|
| *A61B 3/113* | (2006.01) |
| *A63F 13/525* | (2014.01) |
| *A63F 13/5378* | (2014.01) |
| *A63F 13/55* | (2014.01) |
| *G06F 3/01* | (2006.01) |
| *G06T 11/00* | (2006.01) |

(52) U.S. Cl.
CPC ............ *A61B 3/113* (2013.01); *A63F 13/525* (2014.09); *A63F 13/5378* (2014.09); *A63F 13/55* (2014.09); *G06F 3/013* (2013.01); *G06T 11/00* (2013.01)

(58) Field of Classification Search
CPC ........ A63F 13/22; A63F 13/213; G06F 3/013; A61B 3/113
See application file for complete search history.

(56) References Cited

U.S. PATENT DOCUMENTS

| | | | |
|---|---|---|---|
| 10,984,756 B2* | 4/2021 | Tall | G06F 3/013 |
| 2014/0247277 A1 | 9/2014 | Guenter et al. | |
| 2017/0232343 A1* | 8/2017 | Yoshioka | H04N 7/185 463/31 |
| 2017/0285736 A1* | 10/2017 | Young | G06F 3/147 |
| 2018/0059780 A1* | 3/2018 | Mitchell | A63F 13/21 |
| 2018/0205943 A1* | 7/2018 | Trail | G06T 7/73 |
| 2018/0278908 A1 | 9/2018 | Ross | |
| 2018/0357810 A1* | 12/2018 | Young | G06T 15/005 |
| 2019/0026864 A1* | 1/2019 | Chen | G06T 3/4053 |
| 2019/0278090 A1* | 9/2019 | Yehezkel | G06F 3/013 |

(Continued)

FOREIGN PATENT DOCUMENTS

| | | |
|---|---|---|
| GB | 2597917 A | 2/2022 |

OTHER PUBLICATIONS

"International Search Report and Written Opinion", dated Feb. 22, 2024, from the counterpart PCT application PCT/US23/71294.

*Primary Examiner* — Chase E Leichliter
(74) *Attorney, Agent, or Firm* — John L. Rogitz (57) ABSTRACT

A map of a person's spatial vision abilities, including areas of low acuity and areas of high acuity, may be generated from medical records or from a calibration phase. During presentation of a computer simulation such as a computer game, the map is provided to a foveated renderer to optimize which areas should be rendered most crisply. Content placement may be optimized to ensure that any critical elements to the game, for instance, any text that needs to be seen or treasures or special pickups that need to be seen clearly can be moved into regions of the player's field of view that the person has higher acuity in.

20 Claims, 7 Drawing Sheets

(56) References Cited

U.S. PATENT DOCUMENTS

| | | | |
|---|---|---|---|
| 2019/0295507 A1* | 9/2019 | Abuelsaad | A61B 3/111 |
| 2020/0082794 A1* | 3/2020 | Sanders | G06F 3/012 |
| 2022/0101612 A1 | 3/2022 | Palangie et al. | |
| 2022/0160223 A1* | 5/2022 | Bradley | G02B 27/0176 |
| 2022/0225873 A1* | 7/2022 | Arnold | A63F 13/80 |
| 2024/0041319 A1* | 2/2024 | Osman | A63F 13/22 |

* cited by examiner

EYE TRACKING FOR ACCESSIBILITY AND VISIBILITY OF CRITICAL ELEMENTS AS WELL AS PERFORMANCE ENHANCEMENTS

FIELD

The present application relates generally to eye tracking for accessibility and visibility of critical elements as well as performance enhancements

BACKGROUND

There are certain eye conditions that can cause reduced vision in people but only in certain parts of their vision. For example, people with diabetic retinopathy may see some dark spots in parts of their field of view, while others suffering from macular degeneration will have blurriness within certain areas of the field of view. People with glaucoma may similarly have reduced vision across only portions of their field of view.

SUMMARY

Present principles understand that an eye tracker indicates where a person is looking. A model of what that person's vision is, either through a calibration phase or through a transfer of their medical diagnosis into the system, can be used to create a map of which portions of a display the user can see clearly and which they cannot to introduce opportunities for accessibility and optimization.

Accordingly, an assembly includes at least one processor configured with instructions to identify data representing a person's spatially-dependent visual acuity, and using the data, relocate at least one character in at least one computer simulation from a demanded location specified by the computer simulation to an area of at least one display corresponding to an area of first visual acuity as represented by the data and not to an area of the at least one display corresponding to an area of second visual acuity as represented by the data. The first visual acuity is higher than the second visual acuity.

In examples, the computer simulation includes a computer game and the data includes a map.

In some examples, the instructions are executable to implement foveated rendering of the computer simulation based at least in part on the data representing the person's spatially-dependent visual acuity. Accordingly, the instructions may be executable to present a first portion of the computer simulation in a first region of the display with a first resolution responsive to the first region corresponding to an area of first visual acuity as represented by the data representing the person's spatially-dependent visual acuity, and present a second portion of the computer simulation in a second region of the display with a second resolution responsive to the second region corresponding to an area of second visual acuity as represented by the data representing the person's spatially-dependent visual acuity. The first resolution is higher than the second resolution and the first visual acuity is better than the second visual acuity.

In non-limiting implementations the instructions can be executable to determine whether the person is looking at a first location of the display. The instructions may be executable to, responsive to the person not looking at the first location, pause the computer simulation. The instructions further may be executable to, responsive to the person looking at the first location, play the computer simulation. The first location may correspond to a location of a character in the computer simulation. Moreover, the instructions may be executable to, responsive to the person not looking at the first location, filter out of game play or out of presentation on the display at least one in-game event.

In an example embodiment, the instructions are executable to disable at least one eye tracking-operated element responsive to the element being presented in a demanded display region corresponding to poor visual acuity in the data representing the person's spatially-dependent visual acuity.

In another aspect, a device includes at least one computer storage that is not a transitory signal and that in turn includes instructions executable by at least one processor to identify data representing a person's spatially-dependent visual acuity. The instructions are executable to implement foveated rendering of a computer simulation based at least in part on the data representing the person's spatially-dependent visual acuity.

In another aspect, a method includes identifying data representing a person's spatially-dependent visual acuity. The method also includes executing one or both of (a) and (b), in which (a) is using the data representing the person's spatially-dependent visual acuity, relocating at least one character in at least one computer simulation from a demanded location specified by the computer simulation to an area of at least one display corresponding to an area of first visual acuity as represented by the data representing the person's spatially-dependent visual acuity and not to an area of the at least one display corresponding to an area of second visual acuity as represented by the data representing the person's spatially-dependent visual acuity, the first visual acuity being higher than the second visual acuity, and in which (b) is implementing foveated rendering of the computer simulation based at least in part on the data representing the person's spatially-dependent visual acuity.

The details of the present application, both as to its structure and operation, can be best understood in reference to the accompanying drawings, in which like reference numerals refer to like parts, and in which:

DETAILED DESCRIPTION

This disclosure relates generally to computer ecosystems including aspects of consumer electronics (CE) device networks such as but not limited to computer game networks. A system herein may include server and client components which may be connected over a network such that data may be exchanged between the client and server components. The client components may include one or more computing devices including game consoles such as Sony PlayStation® or a game console made by Microsoft or Nintendo or other manufacturer, extended reality (XR) headsets such as virtual reality (VR) headsets, augmented reality (AR) headsets, portable televisions (e.g., smart TVs, Internet-enabled TVs), portable computers such as laptops and tablet computers, and other mobile devices including smart phones and additional examples discussed below. These client devices may operate with a variety of operating environments. For example, some of the client computers may employ, as examples, Linux operating systems, operating systems from Microsoft, or a Unix operating system, or operating systems produced by Apple, Inc., or Google, or a Berkeley Software Distribution or Berkeley Standard Distribution (BSD) OS including descendants of BSD. These operating environments may be used to execute one or more browsing programs, such as a browser made by Microsoft or Google or Mozilla or other browser program that can access websites hosted by the Internet servers discussed below. Also, an operating environment according to present principles may be used to execute one or more computer game programs.

Servers and/or gateways may be used that may include one or more processors executing instructions that configure the servers to receive and transmit data over a network such as the Internet. Or a client and server can be connected over a local intranet or a virtual private network. A server or controller may be instantiated by a game console such as a Sony PlayStation®, a personal computer, etc.

Information may be exchanged over a network between the clients and servers. To this end and for security, servers and/or clients can include firewalls, load balancers, temporary storages, and proxies, and other network infrastructure for reliability and security. One or more servers may form an apparatus that implement methods of providing a secure community such as an online social website or gamer network to network members.

A processor may be a single- or multi-chip processor that can execute logic by means of various lines such as address lines, data lines, and control lines and registers and shift registers.

Components included in one embodiment can be used in other embodiments in any appropriate combination. For example, any of the various components described herein and/or depicted in the Figures may be combined, interchanged, or excluded from other embodiments.

"A system having at least one of A, B, and C" (likewise "a system having at least one of A, B, or C" and "a system having at least one of A, B, C") includes systems that have A alone, B alone, C alone, A and B together, A and C together, B and C together, and/or A, B, and C together.

Figure 1:
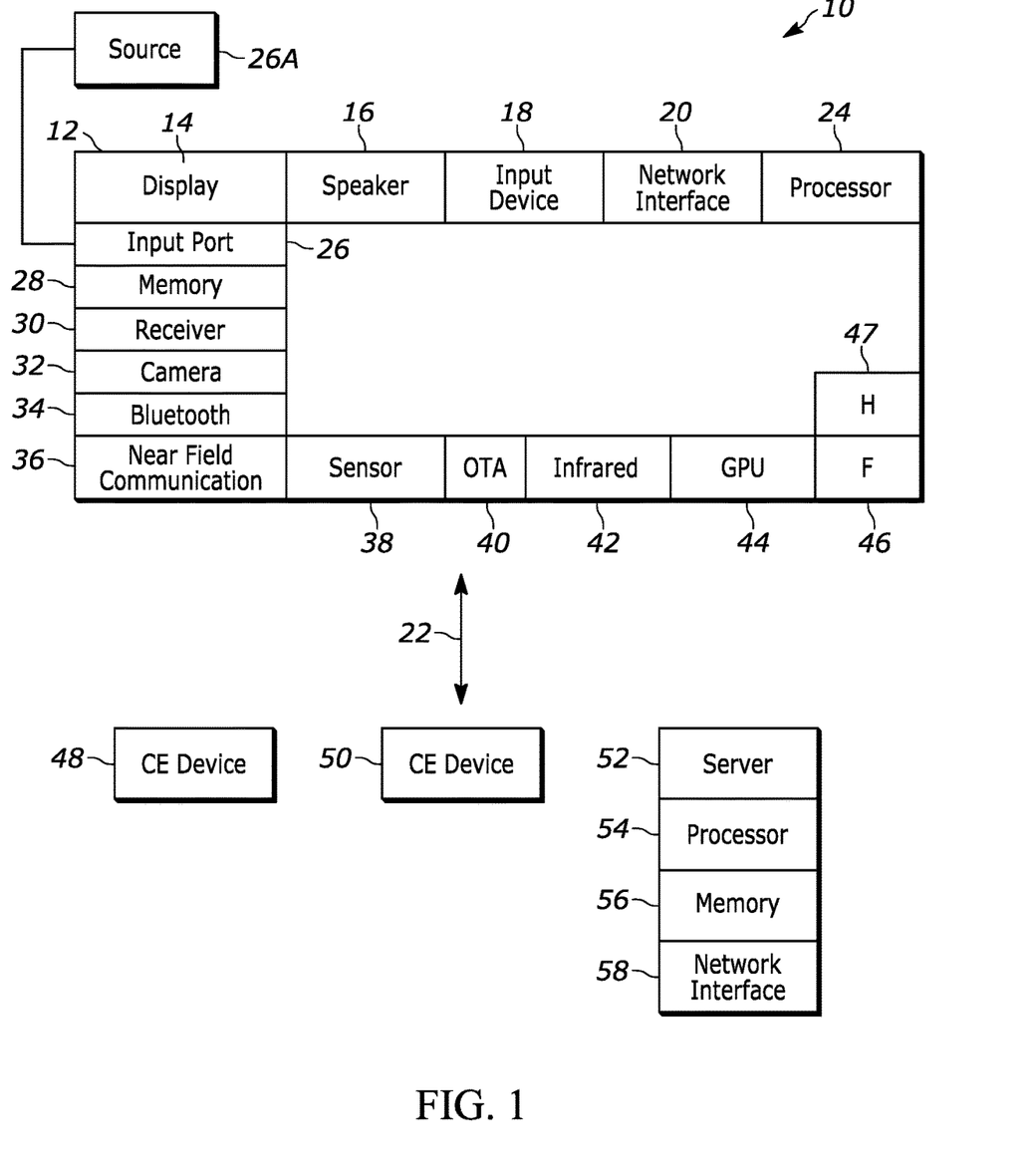
FIG. 1 is a block diagram of an example system in accordance with present principles.

Referring now to FIG. 1, an example system 10 is shown, which may include one or more of the example devices mentioned above and described further below in accordance with present principles. The first of the example devices included in the system 10 is a consumer electronics (CE) device such as an audio video device (AVD) 12 such as but not limited to a theater display system which may be projector-based, or an Internet-enabled TV with a TV tuner (equivalently, set top box controlling a TV). The AVD 12 alternatively may also be a computerized Internet enabled ("smart") telephone, a tablet computer, a notebook computer, a head-mounted device (HMD) and/or headset such as smart glasses or a VR headset, another wearable computerized device, a computerized Internet-enabled music player, computerized Internet-enabled headphones, a computerized Internet-enabled implantable device such as an implantable skin device, etc. Regardless, it is to be understood that the AVD 12 is configured to undertake present principles (e.g., communicate with other CE devices to undertake present principles, execute the logic described herein, and perform any other functions and/or operations described herein).

Accordingly, to undertake such principles the AVD 12 can be established by some, or all of the components shown. For example, the AVD 12 can include one or more touch-enabled displays 14 that may be implemented by a high definition or ultra-high definition "4K" or higher flat screen. The touch-enabled display(s) 14 may include, for example, a capacitive or resistive touch sensing layer with a grid of electrodes for touch sensing consistent with present principles.

The AVD 12 may also include one or more speakers 16 for outputting audio in accordance with present principles, and at least one additional input device 18 such as an audio receiver/microphone for entering audible commands to the AVD 12 to control the AVD 12. The example AVD 12 may also include one or more network interfaces 20 for communication over at least one network 22 such as the Internet, an WAN, an LAN, etc. under control of one or more processors 24. Thus, the interface 20 may be, without limitation, a Wi-Fi transceiver, which is an example of a wireless computer network interface, such as but not limited to a mesh network transceiver. It is to be understood that the processor 24 controls the AVD 12 to undertake present principles, including the other elements of the AVD 12 described herein such as controlling the display 14 to present images thereon and receiving input therefrom. Furthermore, note the network interface 20 may be a wired or wireless modem or router, or other appropriate interface such as a wireless telephony transceiver, or Wi-Fi transceiver as mentioned above, etc.

In addition to the foregoing, the AVD 12 may also include one or more input and/or output ports 26 such as a high-definition multimedia interface (HDMI) port or a universal serial bus (USB) port to physically connect to another CE device and/or a headphone port to connect headphones to the AVD 12 for presentation of audio from the AVD 12 to a user through the headphones. For example, the input port 26 may be connected via wire or wirelessly to a cable or satellite source 26a of audio video content. Thus, the source 26a may be a separate or integrated set top box, or a satellite receiver. Or the source 26a may be a game console or disk player containing content. The source 26a when implemented as a game console may include some or all of the components described below in relation to the CE device 48.

The AVD 12 may further include one or more computer memories/computer-readable storage media 28 such as disk-based or solid-state storage that are not transitory signals, in some cases embodied in the chassis of the AVD as standalone devices or as a personal video recording device (PVR) or video disk player either internal or external to the chassis of the AVD for playing back AV programs or as removable memory media or the below-described server. Also, in some embodiments, the AVD 12 can include a position or location receiver such as but not limited to a cellphone receiver, GPS receiver and/or altimeter 30 that is configured to receive geographic position information from a satellite or cellphone base station and provide the information to the processor 24 and/or determine an altitude at which the AVD 12 is disposed in conjunction with the processor 24.

Continuing the description of the AVD 12, in some embodiments the AVD 12 may include one or more cameras 32 that may be a thermal imaging camera, a digital camera such as a webcam, an IR sensor, an event-based sensor, and/or a camera integrated into the AVD 12 and controllable by the processor 24 to gather pictures/images and/or video in accordance with present principles. Also included on the AVD 12 may be a Bluetooth® transceiver 34 and other Near Field Communication (NFC) element 36 for communication with other devices using Bluetooth and/or NFC technology, respectively. An example NFC element can be a radio frequency identification (RFID) element.

Further still, the AVD 12 may include one or more auxiliary sensors 38 that provide input to the processor 24. For example, one or more of the auxiliary sensors 38 may include one or more pressure sensors forming a layer of the touch-enabled display 14 itself and may be, without limitation, piezoelectric pressure sensors, capacitive pressure sensors, piezoresistive strain gauges, optical pressure sensors, electromagnetic pressure sensors, etc. Other sensor examples include a pressure sensor, a motion sensor such as an accelerometer, gyroscope, cyclometer, or a magnetic sensor, an infrared (IR) sensor, an optical sensor, a speed and/or cadence sensor, an event-based sensor, a gesture sensor (e.g., for sensing gesture command). The sensor 38 thus may be implemented by one or more motion sensors, such as individual accelerometers, gyroscopes, and magnetometers and/or an inertial measurement unit (IMU) that typically includes a combination of accelerometers, gyroscopes, and magnetometers to determine the location and orientation of the AVD 12 in three dimension or by an event-based sensors such as event detection sensors (EDS). An EDS consistent with the present disclosure provides an output that indicates a change in light intensity sensed by at least one pixel of a light sensing array. For example, if the light sensed by a pixel is decreasing, the output of the EDS may be −1; if it is increasing, the output of the EDS may be a +1. No change in light intensity below a certain threshold may be indicated by an output binary signal of 0.

The AVD 12 may also include an over-the-air TV broadcast port 40 for receiving OTA TV broadcasts providing input to the processor 24. In addition to the foregoing, it is noted that the AVD 12 may also include an infrared (IR) transmitter and/or IR receiver and/or IR transceiver 42 such as an IR data association (IRDA) device. A battery (not shown) may be provided for powering the AVD 12, as may be a kinetic energy harvester that may turn kinetic energy into power to charge the battery and/or power the AVD 12. A graphics processing unit (GPU) 44 and field programmable gated array 46 also may be included. One or more haptics/vibration generators 47 may be provided for generating tactile signals that can be sensed by a person holding or in contact with the device. The haptics generators 47 may thus vibrate all or part of the AVD 12 using an electric motor connected to an off-center and/or off-balanced weight via the motor's rotatable shaft so that the shaft may rotate under control of the motor (which in turn may be controlled by a processor such as the processor 24) to create vibration of various frequencies and/or amplitudes as well as force simulations in various directions.

A light source such as a projector such as an infrared (IR) projector also may be included.

In addition to the AVD 12, the system 10 may include one or more other CE device types. In one example, a first CE device 48 may be a computer game console that can be used to send computer game audio and video to the AVD 12 via commands sent directly to the AVD 12 and/or through the below-described server while a second CE device 50 may include similar components as the first CE device 48. In the example shown, the second CE device 50 may be configured as a computer game controller manipulated by a player or a head-mounted display (HMD) worn by a player. The HMD may include a heads-up transparent or non-transparent display for respectively presenting AR/MR content or VR content (more generally, extended reality (XR) content). The HMD may be configured as a glasses-type display or as a bulkier VR-type display vended by computer game equipment manufacturers.

In the example shown, only two CE devices are shown, it being understood that fewer or greater devices may be used. A device herein may implement some or all of the components shown for the AVD 12. Any of the components shown in the following figures may incorporate some or all of the components shown in the case of the AVD 12.

Now in reference to the afore-mentioned at least one server 52, it includes at least one server processor 54, at least one tangible computer readable storage medium 56 such as disk-based or solid-state storage, and at least one network interface 58 that, under control of the server processor 54, allows for communication with the other illustrated devices over the network 22, and indeed may facilitate communication between servers and client devices in accordance with present principles. Note that the network interface 58 may be, e.g., a wired or wireless modem or router, Wi-Fi transceiver, or other appropriate interface such as, e.g., a wireless telephony transceiver.

Accordingly, in some embodiments the server 52 may be an Internet server or an entire server "farm" and may include and perform "cloud" functions such that the devices of the system 10 may access a "cloud" environment via the server 52 in example embodiments for, e.g., network gaming applications. Or the server 52 may be implemented by one or more game consoles or other computers in the same room as the other devices shown or nearby.

The components shown in the following figures may include some or all components shown in herein. Any user interfaces (UI) described herein may be consolidated and/or expanded, and UI elements may be mixed and matched between UIs. The logic shown in flow charts herein may be executed by any one or more of the processors discussed herein.

Present principles may employ various machine learning models, including deep learning models. Machine learning models consistent with present principles may use various algorithms trained in ways that include supervised learning, unsupervised learning, semi-supervised learning, reinforcement learning, feature learning, self-learning, and other forms of learning. Examples of such algorithms, which can be implemented by computer circuitry, include one or more neural networks, such as a convolutional neural network (CNN), a recurrent neural network (RNN), and a type of RNN known as a long short-term memory (LSTM) network. Support vector machines (SVM) and Bayesian networks also may be considered to be examples of machine learning models. In addition to the types of networks set forth above, models herein may be implemented by classifiers.

As understood herein, performing machine learning may therefore involve accessing and then training a model on training data to enable the model to process further data to make inferences. An artificial neural network/artificial intelligence model trained through machine learning may thus include an input layer, an output layer, and multiple hidden layers in between that that are configured and weighted to make inferences about an appropriate output.

Figure 2:
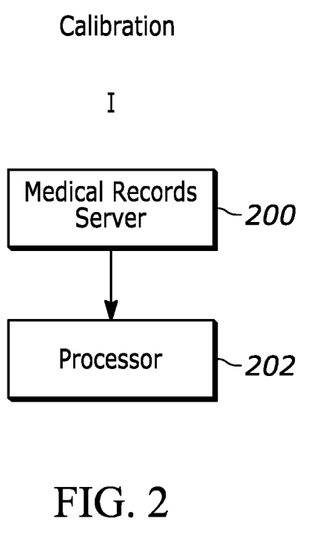
FIG. 2 illustrates a block diagram of a first example method for obtaining a map of a person's visual acuity.

FIG. 2 illustrates a first technique for obtaining information related to a person's vision. A medical records server 200 provides the data to a processor 202 such as any processor or device disclosed herein. The information indicates a person's field of view and within that field of view areas of high, average, and low visual acuity. The information thus establishes a map.

Figure 3:
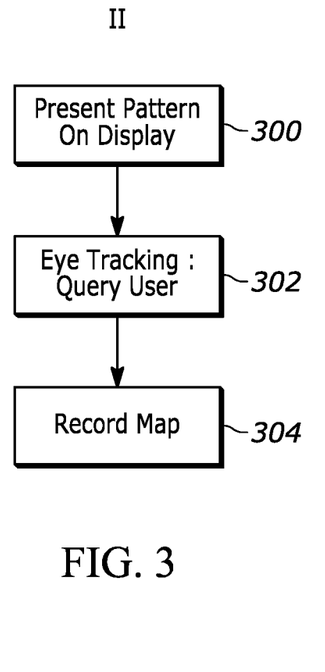
FIG. 3 illustrates example logic in example flow chart format of a second example method for obtaining a map of a person's visual acuity.
Figure 4:
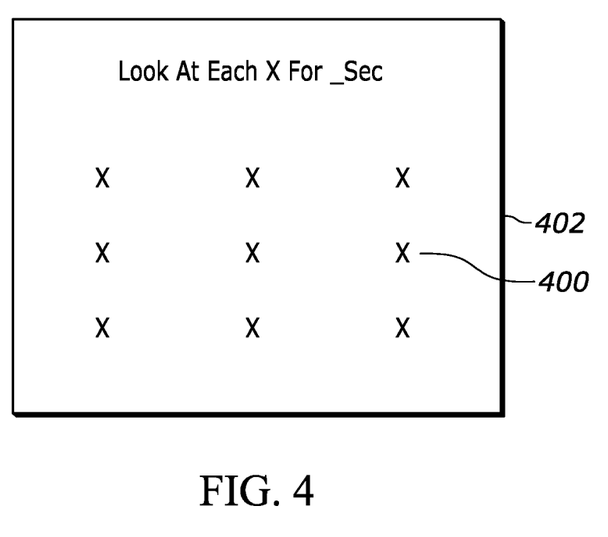
FIG. 4 illustrates an example screen shot of an example user interface (UI) that may be presented on any display discussed herein related to the technique of FIG. 3.

FIG. 3 indicates that in addition or alternatively, the map data can be obtained by presented a pattern on a display at block 300. FIG. 4 illustrates such a pattern 400 presented on a display 402 such as any display divulged herein. A prompt 404 may be presented visually or audibly for the person whose vision is being mapped to look at each element in the pattern that the person can see for a threshold period. The person's eyes are tracked at block 302, and dwell times noted. The areas in which the person's vision dwelt for the threshold period are identified as areas of good visual acuity. Areas the person's eyes did not dwell in are identified as poor visual acuity, and based on these identifications a map is generated and recorded at block 304.

Note that a person may be permitted to define a "dominant" portion of eyesight using a computer input device. For instance, it can be assumed that where the person looks is dominant because that's probably where the person is foveating, but the person may relocate that dominant region if desired.

In an alternate technique the person may be instructed to look straight ahead, at the center of the display 402, and using peripheral vision touch areas on the screen in which pattern elements can be discerned. Areas touched are mapped to areas of good visual acuity.

Figure 5:
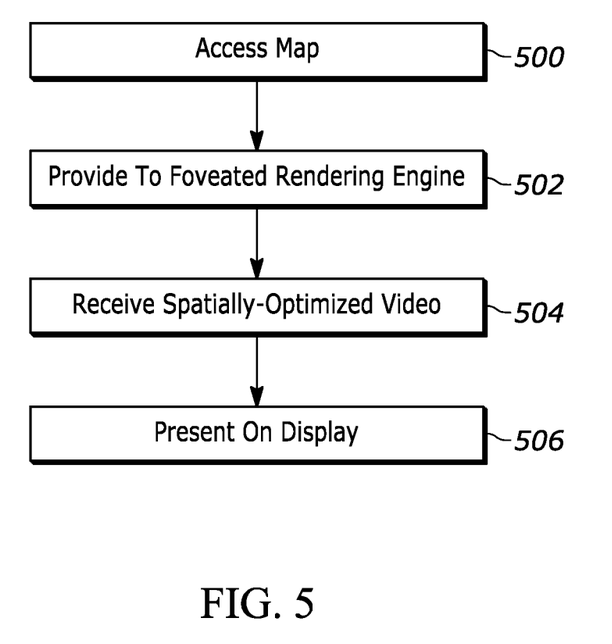
FIG. 5 illustrates example logic in example flow chart format of logic consistent with present principles.

Refer now to FIG. 5. Commencing at block 500, the map of the person's visual acuity is accessed. Moving to block 502, this map is provided to a foveated renderer to optimize which areas should be rendered most crisply. Present principles understand that a person suffering from glaucoma can actually have a very good VR experience because a foveated renderer can put many more resources to the limited areas that the person can see so that the person may be presented with much crisper images than people with normal vision. Granted their overall field of vision is different, however they can see very sharp images in areas that they can see well.

Proceeding to block 504, spatially-optimized video is received which has been optimized as discussed above to place high resolution video in high visual acuity regions of the display that correspond to high visual acuity areas of the map of the person's vison. The spatially-optimized video is presented on a display at block 506.

Figure 6:
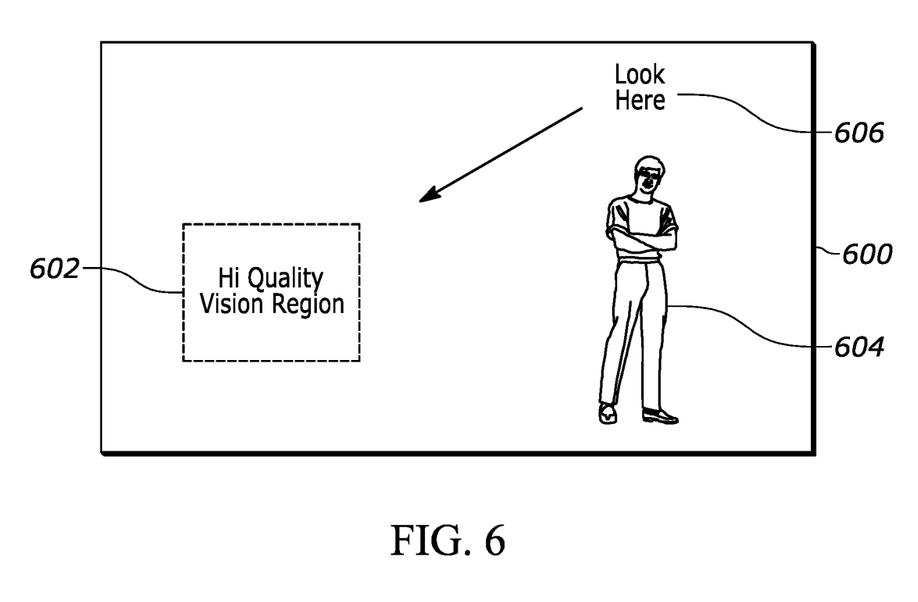
FIG. 6 illustrates an example screen shot of an example computer simulation such as a computer game that may be presented on any display discussed herein related to the technique of FIG. 5.

FIG. 6 illustrates a display 600 in which high resolution video is presented in a high-quality region 602 consistent with present principles, with lower quality or no video being presented in regions outside the region(s) 602. Or, should the person's visual acuity map indicate that the person has poor but some vision such as blurry vision outside the high visual acuity areas, lower resolution video with color contrast between objects increased from demanded contrast may be presented as indicated at 604 in FIG. 6 to indicate critical video objects instead of just blanking out all video completely in such regions. A prompt 606 also may be presented in regions corresponding to lower visual acuity to direct the person to look at regions corresponding to higher visual acuity for that person.

Figure 7:
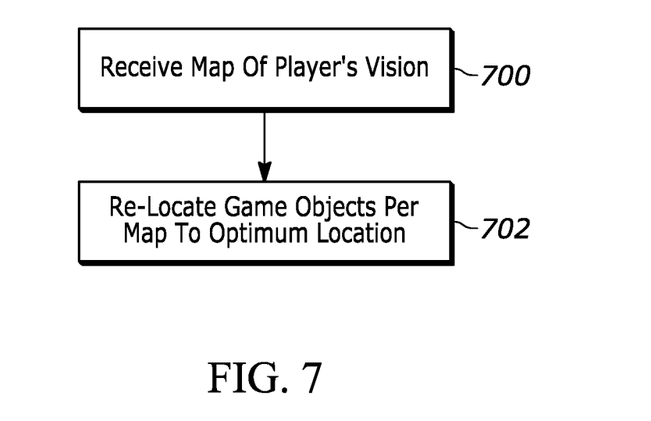
FIG. 7 illustrates example logic in example flow chart format of further logic consistent with present principles.
Figure 8:
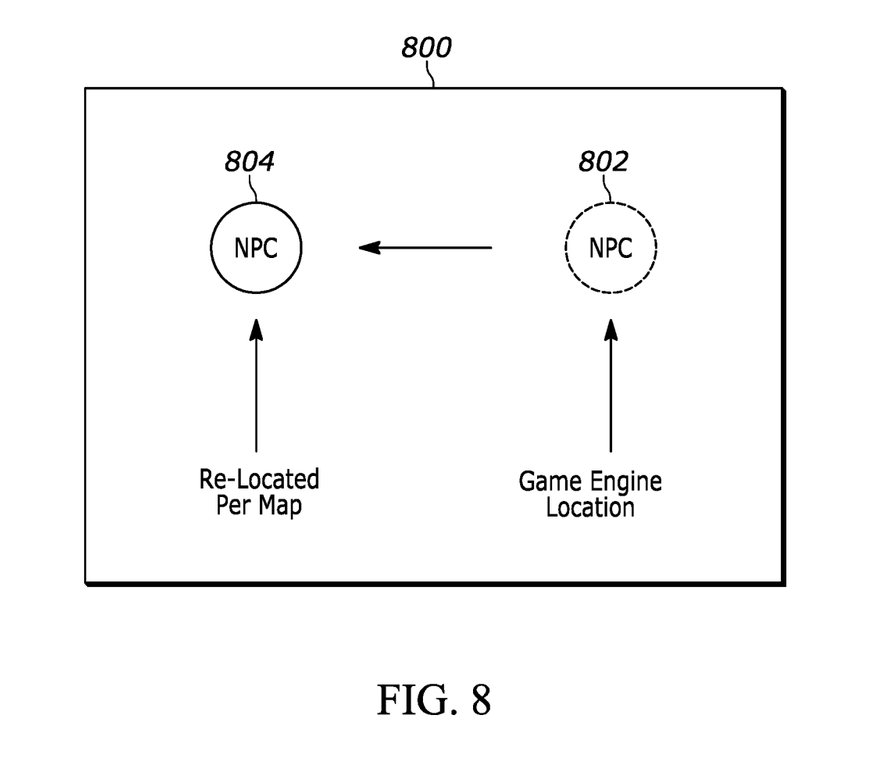
FIG. 8 illustrates an example screen shot of an example computer simulation such as a computer game that may be presented on any display discussed herein related to the technique of FIG. 7.

Refer now to FIGS. 7 and 8 in which content placement is optimized. Beginning at block 700, the map of the player's visual acuity is received or accessed. The logic then moves to block 702 to ensure that any critical elements in a computer simulation such as a computer game, for instance, any text that needs to be seen or treasures or special pickups that need to be seen clearly, or critical heads-up display elements such as crosshairs, is moved from frame locations demanded by the game engine into regions corresponding to high visual acuity as indicated by the map.

FIG. 8 illustrates an example of this. In the example shown, a non-player character (NPC) is to be presented on a display 800 at a demanded display area 802. However, because the map of the person's visual acuity indicates poor vision in this area, the NPC is not presented in the demanded display area 802 but rather in at a relocation region 804 corresponding to an area of good visual acuity in the person's visual acuity map.

Figure 9:
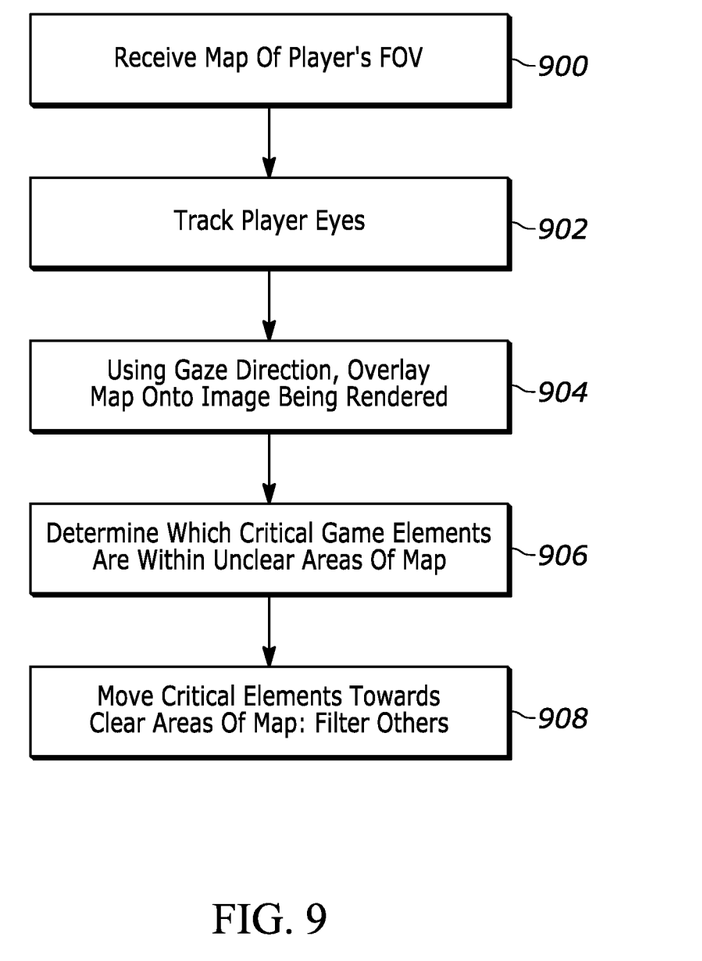
FIG. 9 illustrates further example logic in example flow chart consistent with present principles.

FIG. 9 illustrates further. Commencing at block 900, the map of the person's visual acuity is received/accessed, indicating the areas the person can see well in and those the person cannot see well. Proceeding to block 902, an eye tracker (typically including one or more cameras feeding images to one or more ML models trained to track the direction of gaze of the pupils) is used to track the position of a player's eyes (for instance in a VR environment) during gameplay.

Moving to block 904, the processor executing the game engine receives the gaze direction and uses it to overlay the person's vision map onto the rendered image. At block 906 the processor executing the game engine measures the level to which critical elements on the rendered image (heads-up display (HUD), text, treasures, etc.) fall within the unclear areas of the player's vision as indicated by the map. Proceeding to block 908 the processor executing the game engine adjusts the position of critical elements that fall outside of the clear (good visual acuity) regions by moving them towards the clear regions.

Figure 10:
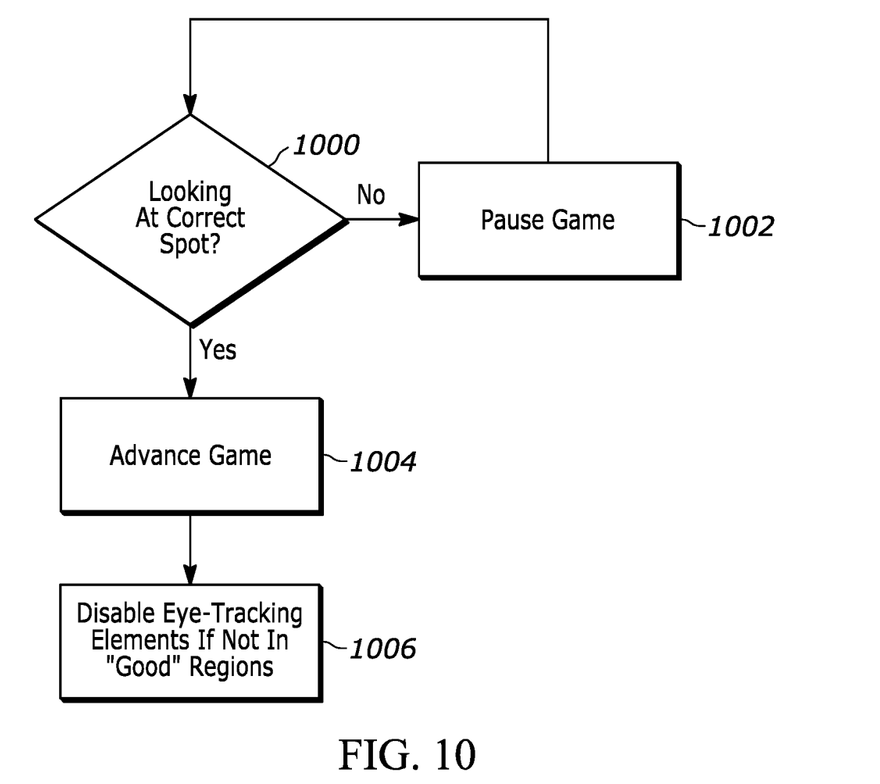
FIG. 10 illustrates yet further example logic in example flow chart consistent with present principles.

FIG. 10 illustrates additional techniques consistent with present principles. Decision diamond 1000 indicates that using eye tracking, it is determined whether the person is looking at a correct location in the current game context, such as the location of an important game character. If not, the game may be paused at state 1002 to allow the person time to divert his or her gaze to the correct spot. During this period, the simulation may present audible and/or visual and/or tactile hints to the user based on heuristics to determine what kind of hints to give. For instance, if the person never saw a critical element, the hint generator may try to draw the person's attention to that region of the screen so the person can "discover" the object. Conversely, if the person saw the object but didn't realize that he or she was supposed to interact with it, the hint generator may highlight or suggest that the person interact with the object. A hint generator may consider an objects "seen" if the object was seen by a clear portion of the person's vision.

Also, if desired certain in-game events may be filtered out of game play or at least out of presentation on the display if the processor executing eye tracking determines that the person cannot see the game events.

Figure 11:
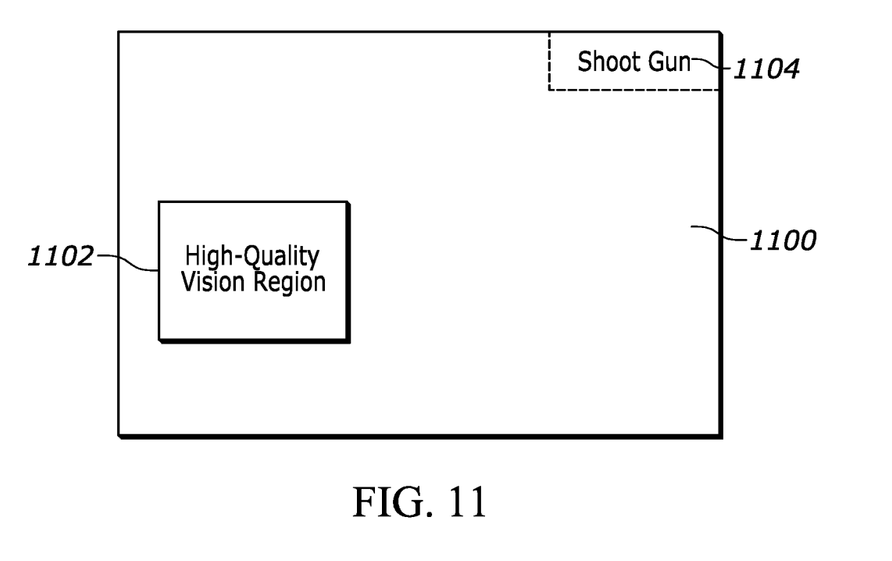
FIG. 11 illustrates an example screen shot of an example computer simulation such as a computer game that may be presented on any display discussed herein related to the technique of FIG. 10.

Once the person is looking at the correct location the game may be advanced once again at state 1004. Moreover, block 1006 indicates that if desired, certain eye tracking-operated elements can be disabled if they are presented in a display region corresponding to poor visual acuity on the person's visual acuity map. FIG. 11 illustrates this, in which a display 1100 presents game video in a high quality region 1102 corresponding to an area of good visual acuity on the person's visual acuity map and does not present or grays out (as indicated by the dashed lines) a selector 1104, in the example shown, to shoot a virtual gun by gazing at the selector 1104 for a threshold period.

Figure 12:
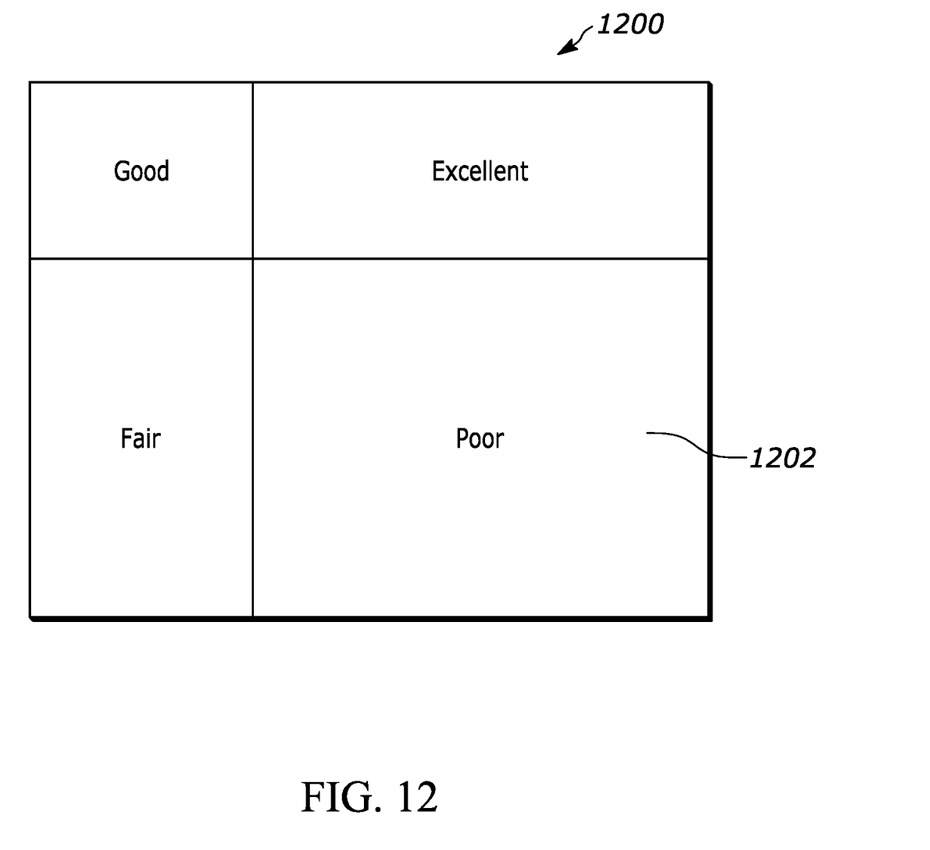
FIG. 12 illustrates an example visual acuity map.

FIG. 12 illustrates a non-limiting example of a person's visual acuity map 1200. In the example shown, areas 1202 are designated using relative terms to indicate the person's visual acuity in that respective area, it being understood that the center of the map 1200 corresponds the center of the person's field of view when looking straight ahead. Although FIG. 4 shows four relative indicators, only two may be used, i.e., good and bad. When more than two relative indicators are used, the game engine may preferentially present the most critical video first in the area corresponding to the best indicator, then less critical video in the area corresponding to the next best indicator, and perhaps little or no video in the remaining regions. Along the same lines, the highest resolution video may be presented in the area corresponding to the best visual acuity, the next highest resolution may be used to present video in the next best visual acuity area, and so on, with the lowest resolution video being presented in the area corresponding to the worst visual acuity. Thus, more than two resolutions may be used to present video in more than two display regions based on visual acuity of a person in those regions.

While the particular embodiments are herein shown and described in detail, it is to be understood that the subject matter which is encompassed by the present invention is limited only by the claims.

What is claimed is:

1. An assembly, comprising:
   at least one processor system configured with instructions to:
   identify data representing a person's spatially-dependent visual acuity; and
   using the data, relocate at least one character in at least one computer simulation from a demanded location specified by the computer simulation to an area of at least one display corresponding to an area of first visual acuity as represented by the data and not to an area of the at least one display corresponding to an area of second visual acuity as represented by the data, the first visual acuity being higher than the second visual acuity.

2. The assembly of claim 1, wherein the computer simulation comprises a computer game.

3. The assembly of claim 1, wherein the data comprises a map.

4. The assembly of claim 1, wherein the instructions are executable to:
   implement foveated rendering of the computer simulation based at least in part on the data representing the person's spatially-dependent visual acuity.

5. The assembly of claim 4, wherein the instructions are executable to:
   present a first portion of the computer simulation in a first region of the display with a first resolution responsive to the first region corresponding to an area of first visual acuity as represented by the data representing the person's spatially-dependent visual acuity; and
   present a second portion of the computer simulation in a second region of the display with a second resolution responsive to the second region corresponding to an area of second visual acuity as represented by the data representing the person's spatially-dependent visual acuity, the first resolution being higher than the second resolution, the first visual acuity being better than the second visual acuity.

6. The assembly of claim 1, wherein the instructions are executable to:
   determine whether the person is looking at a first location of the display;
   responsive to the person not looking at the first location, pause the computer simulation;
   responsive to the person looking at the first location, play the computer simulation.

7. The assembly of claim 6, wherein the first location corresponds to a location of a character in the computer simulation.

8. The assembly of claim 6, wherein the instructions are executable to:
   responsive to the person not looking at the first location, filter out of game play or out of presentation on the display at least one in-game event.

9. The assembly of claim 1, wherein the instructions are executable to:
   disable at least one eye tracking-operated element responsive to the element being presented in a demanded display region corresponding to poor visual acuity in the data representing the person's spatially-dependent visual acuity.

10. A device, comprising:
    at least one computer storage that is not a transitory signal and that comprises instructions executable by at least one processor system to:
    identify data representing a person's spatially-dependent visual acuity; and
    using the data representing the person's spatially-dependent visual acuity, relocate at least one character in the computer simulation from a demanded location specified by the computer simulation to an area of at least one display corresponding to an area of first visual acuity as represented by the data and not to an area of the at least one display corresponding to an area of second visual acuity as represented by the data, the first visual acuity being higher than the second visual acuity.

11. The device of claim 10, wherein the instructions are executable to:
    present a first portion of the computer simulation in a first region of the display with a first resolution responsive to the first region corresponding to an area of first visual acuity as represented by the data representing the person's spatially-dependent visual acuity; and
    present a second portion of the computer simulation in a second region of the display with a second resolution responsive to the second region corresponding to an area of second visual acuity as represented by the data representing the person's spatially-dependent visual acuity, the first resolution being higher than the second resolution, the first visual acuity being better than the second visual acuity.

12. The device of claim 10, wherein the instructions are executable to:
    determine whether the person is looking at a first location of the display;
    responsive to the person not looking at the first location, pause the computer simulation;

responsive to the person looking at the first location, play the computer simulation.

13. The device of claim 12, wherein the first location corresponds to a location of a character in the computer simulation.

14. The device of claim 12, wherein the instructions are executable to:

responsive to the person not looking at the first location, filter out of game play or out of presentation on the display at least one in-game event.

15. The device of claim 10, wherein the instructions are executable to:

disable at least one eye tracking-operated element responsive to the element being presented in a demanded display region corresponding to poor visual acuity in the data representing the person's spatially-dependent visual acuity.

16. The device of claim 10, wherein the instructions are executable to:

implement foveated rendering of a computer simulation based at least in part on the data representing the person's spatially-dependent visual acuity.

17. The device of claim 10, wherein the computer simulation comprises a computer game.

18. The device of claim 10, wherein the data representing the person's spatially-dependent visual acuity comprises a map.

19. A method, comprising:

identifying data representing a person's spatially-dependent visual acuity; and (a) using the data representing the person's spatially-dependent visual acuity, relocating at least one character in at least one computer simulation from a demanded location specified by the computer simulation to an area of at least one display corresponding to an area of first visual acuity as represented by the data representing the person's spatially-dependent visual acuity and not to an area of the at least one display corresponding to an area of second visual acuity as represented by the data representing the person's spatially-dependent visual acuity, the first visual acuity being higher than the second visual acuity.

20. The method of claim 19, wherein the computer simulation comprises a computer game.

* * * * *